(12) United States Patent
Psarrakis et al.

(10) Patent No.: US 9,050,307 B2
(45) Date of Patent: Jun. 9, 2015

(54) METHOD FOR THE PREPARATION OF A LEVOTHYROXINE SOLUTION

(75) Inventors: Yannis Psarrakis, Lavrion-Attica (GR); Konstantinos I. Lioumis, Lavrion-Attica (GR)

(73) Assignee: EMP Pharma GmbH (CH)

( * ) Notice: Subject to any disclaimer, the term of this patent is extended or adjusted under 35 U.S.C. 154(b) by 149 days.

(21) Appl. No.: 14/003,598

(22) PCT Filed: Mar. 10, 2011

(86) PCT No.: PCT/IB2011/051015
§ 371 (c)(1),
(2), (4) Date: Nov. 15, 2013

(87) PCT Pub. No.: WO2012/120338
PCT Pub. Date: Sep. 13, 2012

(65) Prior Publication Data
US 2014/0073695 A1 Mar. 13, 2014

(51) Int. Cl.
*A61K 31/198* (2006.01)
*A61K 9/08* (2006.01)
*A61K 31/055* (2006.01)

(52) U.S. Cl.
CPC .............. *A61K 31/198* (2013.01); *A61K 9/08* (2013.01); *A61K 31/055* (2013.01)

(58) Field of Classification Search
CPC ...... A61K 31/055; A61K 31/198; A61K 9/08
See application file for complete search history.

(56) References Cited

U.S. PATENT DOCUMENTS

| | | | |
|---|---|---|---|
| 3,035,974 A | 5/1962 | Israel | |
| 6,458,842 B1 * | 10/2002 | Dickinson et al. | 514/567 |
| 2004/0266877 A1 | 12/2004 | Dickinson et al. | |
| 2005/0059574 A1 | 3/2005 | Klein et al. | |

FOREIGN PATENT DOCUMENTS

| | | |
|---|---|---|
| GB | 2191695 A | 12/1987 |
| WO | WO-2007/077252 A1 | 7/2007 |

OTHER PUBLICATIONS

Won, C.M. "Kinetics of Degradation of Levothyroxine in Aqueous Solution and in Solid State" Pharmaceutical Research, vol. 9, No. 1, 1992.*
Patel, H.; Stalcup, A.; Dansereau, R.; Sakr, A. "The effect of excipients on the stability of levothyroxine sodium pentahydrate tablets" International Journal of Pharmaceutics 264 (2003) 35-43.*
"International Application No. PCT/IB2011/051015, International Search Report and Written Opinion mailed Mar. 7, 2012", 11 pgs.
Strong, D. K., et al., "Stability of Levothyroxine in Sodium Chloride for IV Administration", Can J Hosp Pharm., 63(6), (Nov.-Dec. 2010), 437-443.
Won, C. M, "Kinetics of degradation of levothyroxine in aqueous solution and in solid state", Pharm Res., 9(1), (1992), 131-7.

* cited by examiner

*Primary Examiner* — Sean Basquill
*Assistant Examiner* — Andrew S Rosenthal
(74) *Attorney, Agent, or Firm* — Schwegman Lundberg & Woessner, P.A.

(57) ABSTRACT

Levothyroxine, also known as L-thyroxine, synthetic T4, or 3,5,3',5'-tetraiodo-L-thyronine, CAS number 51-48-9, is a synthetic form of thyroxine, used as a hormone substitute for patients with thyroid conditions. The invention relates to a method for the preparation of an oral levothyroxine composition. The method according to the invention results in liquid levothyroxine formulations that have improved storage stability compared to known liquid levothyroxine formulations.

15 Claims, No Drawings

METHOD FOR THE PREPARATION OF A LEVOTHYROXINE SOLUTION

PRIORITY CLAIM TO RELATED APPLICATIONS

This application is a national stage application under 35 U.S.C. §371 of PCT/IB2011/051015, filed Mar. 10, 2011, and published as WO 2012/120338A1 on Sep. 13, 2012, which application and publication are incorporated by reference as if reproduced herein and made a part hereof in their entirety, and the benefit of priority of each of which is claimed herein.

FIELD OF THE INVENTION

The invention relates to a method for the preparation of an oral levothyroxine composition.

BACKGROUND OF THE INVENTION

Levothyroxine, also known as L-thyroxine, synthetic T4, or 3,5,3',5'-tetraiodo-L-thyronine, CAS number 51-48-9, is a synthetic form of thyroxine, used as a hormone substitute for patients with thyroid conditions, such as hypothyroidism, as well as conditions in which the thyroid gland becomes enlarged, causing swelling of the neck.

Thyroid hormones regulate multiple metabolic processes and play an essential role in normal growth and development, and normal maturation of the central nervous system and bone. Levothyroxine sodium was initially manufactured as synthetic T4 in 1958 and it was first introduced into the market as early as before 1962 without an approved NDA, apparently in the belief that it was not a new drug.

Levothyroxine sodium is very slightly soluble in water and slightly soluble in ethanol (96 percent). Levothyroxine sodium is described in the European Pharmacopoeia. The chemical designation of Levothyroxine sodium is Sodium (2S)-2-amino-3-[4-(4-hydroxy-3,5-diiodophenoxy)-3,5-diiodophenyl]propanoate. Its molecular formula is $C_{15}H_{10}I_4NnaO_4$, $xH_2O$ and its molecular weight is 799 (anhydrous substance). The structural formula is:

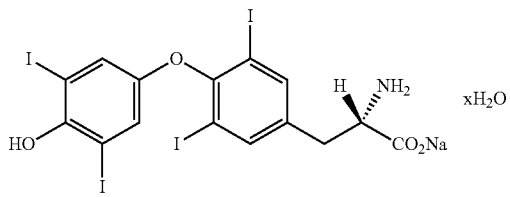

Orally administered levothyroxine sodium is used as replacement therapy in conditions characterized by diminished or absent thyroid function such as cretinism, myxedema, non-toxic goiter, or hypothyroidism (Food and Drug Administration 1997; Wertheimer and Santella 2005).

Levothyroxine Sodium Oral Solution is indicated for:
hypothyroidism (congenital or acquired)
diffuse non toxic goitre or Hashimoto's thyroiditis
thyroid carcinoma The treatment of any thyroid disorder should be determined on an individual basis, taking account of clinical response, biochemical tests and regular monitoring. A pretherapy ECG is valuable as changes induced by hypothyroidism may be confused with evidence of ischaemia. If too rapid an increase of metabolism is produced (causing diarrhoea, nervousness, rapid pulse, insomnia, tremors and sometimes anginal pain where there is latent myocardial ischaemia), reduce the dose or withhold for 1-2 days and start again at a lower dose.

Oral solutions of levothyroxine are particularly suitable for use in children and in the elderly who may have difficulty to swallow tablets. Unfortunately, solutions of levothyroxine are less stable compared to tablets during storage. Also, levothyroxine solutions may comprise relatively high amounts of liothyronine, which is believed to be the source of side-effects in certain patients. Aqueous levothyroxine solutions are prone to decomposition compared to the solid forms. The big advantage of the solution is the uniformity of dosage units in comparison to solid dosage forms (tablets). The tablets, usually due to the very low levothyroxine content (0.04% up to 0.5% w/w), have problems of content uniformity during the production process and many times the actual content that the patient receives with tablet therapy, is not 100% but could range from 85% up to 120% and this creates serious problems on patient treatment. In contrast, it is much easier to obtain a homogeneous solution.

OBJECT AND SUMMARY OF THE INVENTION

It is an object of the invention to provide a more stable levothyroxine solution. It is another object of the solution to provide a levothyroxine solution that comprises less liothyronine. It is yet another object of the invention to enable a faster method for the preparation of oral levothyroxine solutions.

The invention provides a method for the preparation of an oral levothyroxine composition, comprising the steps of:
a) providing a salt of levothyroxine, preferably the sodium salt of levothyroxine
b) mixing levothyroxine with an aqueous solvent,
c) adjusting the pH to a pH of at least 8 to yield a basic aqueous solvent, and
d) dissolving the levothyroxine in the basic aqueous solvent to yield a levothyroxine solution, and
e) lowering the pH of the clear levothyroxine solution to between 5-6, preferably to about 5.5.

Surprisingly, this method results in a levythyroxine solution which is more stable during storage. The obtained solution also comprises less liothyronine. Also, the preparation is relatively fast; in particular the dissolving of levothyroxine in the basic aqueous solvent is relatively fast compared to dissolving in neutral or acidic water (pH<7) or aqueous solvents of otherwise the same composition.

The provided levothyroxine salt and other ingredients are all of pharmaceutical quality. The pH is determined and monitored, preferably using a calibrated electronic pH meter based on electrode potential. In order to determine the pH during adjusting the pH, the pH should be adjusted by adding small amounts of base to the mixture while stirring, and allowing to homogenize and stabilize the measured pH before proceeding to further adjust the pH. The end pH 5-6 is suitable for storage as well as for administering the levothyroxine solution to a patient. As levothyroxine may show degradation under the influence of UV and blue light, the process is preferably performed in the dark or in dark glass comprising a UV-filter.

Best results are obtained when in step c) the pH is adjusted to from 9 to 11, preferably to about 10.

It is preferred if the adjusting of the pH was done by adding a base. It is preferred if the base is added as an aqueous solution, for instance with a concentration in the order of 0.1-2 mol/l. Suitable bases comprise Potassium Bicarbonate, Potassium Citrate, Potassium Citrate, Potassium Hydroxide, Sodium Carbonate, Calcium Hydroxide, Ammonia Solution, Sodium Hydroxide, Sodium Borate, Monoethanolamine, Sodium Citrate Dihydrate, Diethanolamine, Triethanolamine and Sodium Bicarbonate. Preferably, the added base is a sodium hydroxide solution. Adding sodium hydroxide is pharmaceutically acceptable base which yielded a stable solution.

Advantageously, the adjusting of the pH in step e) was done using a carboxylic acid. Carboxylic acids, preferably water-soluble carboxylic acids, showed a good stability. Suitable carboxylic acids comprise Lauric Acid, Tartaric Acid, Acetic Acid, Glacial, Maleic Acid, and Sorbic Acid. In a preferred embodiment, the carboxylic acid is citric acid, which was well tolerated, compatible with levothyroxine and gave good results.

It is preferred if the aqueous solvent was a mixture of water and a water-miscible organic solvent or solubilizer. Water miscible organic solvents improved the speed of dissolving and gave a stable solution. Preferably the water-miscible organic solvent comprises glycol. Suitable organic solvents or solubilizers comprise Acetone, Alcohol, Benzyl Alcohol, Benzyl Benzoate, Butylene Glycol, Dibutyl Phthalate, Diethyl Phthalate, Dimethyl Phthalate, Dimethyl Sulfoxide, Dimethylacetamide, Glycofurol, Glycerin, Isopropyl Alcohol, Isopropyl Myristate, Isopropyl Palmitate, Polyethylene Glycol, Propylene Carbonate, Pyrrolidone, Triacetin, Triethyl Citrate and Triolein. In a preferred embodiment, the ratio between water and glycol was in the range of 10:1 to 1:10.

It is preferred if, in step b), levothyroxine is mixed with the aqueous solvent while heating the mixture to 30-70° C., preferably from 40-50° C., more preferably from 40-45° C. Raising the temperature significantly speeded up the dissolving of levothyroxine. Too high a temperature may however give rise to an increase in degradation products and lower stability of the final product.

Advantageously, also a preservative is added to the aqueous solvent. This yield an increased stability during storage. Suitable preservatives comprise Bronopol, Imidurea, Potassium Sorbate, Phenoxyethanol, Phenylmercuric Acetate, Butylparaben, Benzyl Alcohol, Phenylmercuric Borate, Chlorocresol, Benzethonium Chloride, Phenylethyl Alcohol, Benzalkonium Chloride, Methylparaben, Hexetidine, Chlorobutanol, Ethylparaben, Propylparaben, Sodium Benzoate, Potassium Benzoate, Sorbic Acid, Cresol, Propylparaben Sodium, Cetylpyridinium Chloride, Phenylmercuric Nitrate, Chloroxylenol, Propionic Acid, Phenol, Thimerosal, Sulfur Dioxide, Boric Acid, Edetic Acid, Sodium Propionate, Calcium Chloride, Sodium Acetate, Sodium Sulfite, Benzoic Acid, Monothioglycerol, Cetrimide, Calcium Acetate, Butylene Glycol, Sodium Metabisulfite, Alcohol, Propyl Gallate, Potassium Metabisulfite, Sodium Lactate, Chlorhexidine, Calcium Lactate, Pentetic Acid, Glycerin, Propylene Glycol Alginate, Sodium Borate, Magnesium Trisilicate, Isopropyl Alcohol, Dimethyl Ether, Propylene Glycol, Butylated Hydroxyanisole, Pyrrolidone, Lactic Acid, Sodium Lauryl Sulfate and Dimethyl Sulfoxide. Preferably, the preservative is sodium methylparaben, which showed a good compatibility with levothyroxine.

The invention further provides a liquid oral Levothyroxine composition obtainable using the method according to invention.

Preferably, the composition comprises a sodium levothyroxine concentration of approximately 25 μg in 5 ml, approximately 50 μg in 5 ml or approximately 100 μg in 5 ml.

In a preferred embodiment the composition comprises sodium levothyroxine, glycerol, water and a preservative.

In a preferred embodiment, the Oral Levothyroxine composition is packed in a unit dose system selected from the group consisting of ampoules, sachets, vial, s blister packs, tubes, of stick packs, wherein the unit dose is arranged to deliver separate doses of levothyroxine from 25 up to 300 mcg per single dose.

DESCRIPTION OF PREFERRED EMBODIMENTS

The invention will now be elucidated by the following non-limiting embodiments.

Process Description

As L-Thyroxine may degrade under the influence of light, the process was performed shielded from direct sunlight. The process was otherwise performed using regular manufacturing equipment. The basic steps are as follows:

After weighing the excipients and the active ingredient, a premix was prepared by dispersing the sodium salt of L-thyroxine (Levothyroxine sodium) in glycerol, in the ratio of 1 part of levothyroxine and 100 parts of glycerol by weight. Optionally, already part of the water may be added in this premix step, keeping the amount of water below the amount of glycerol. The dispersion is agitated and heated for 15-30 minutes while maintaining the temperature between 40 and 50° C., during which part of the L-thyroxine Na dissolves. In a separate vessel, the remaining amount of water was stirred while adding 1N NaOH solution in water until a pH of approximately 10 was obtained. This basic solution was added to the partly dissolved L-Thyroxine Na dispersion. The final mixture was stirred at room temperature (20-25° C.) until a clear homogeneous solution was obtained.

To the clear solution of L-Thyroxine Na in glycerol/water, Nipagin M Sodium (sodium methylparaben) was added while stirring until a clear solution was obtained. The remaining amount of glycerol was subsequently added until a clear solution was obtained.

After that, the pH of the solution was adjusted to approximately 5.5 by adding citric acid, and the volume was adjusted to the predetermined L-thyroxine concentration by adding minor amounts water. The final solution was filtered over a 1 μm filter, and filled in light-protective containers, such as amber type III glass 100 ml bottles sealed with child resistant, tamper evident screw caps.

Preferably, the doses of levothyroxine are packed in dose units or monodose delivery systems of the levothyroxine solution. Such systems comprise sealed vessels holding dosed units mentioned above. The vessels are made for instance of PVC or PVDC or composite materials comprising plastic materials reinforced with aluminum and/or glass layers for a better protection from are and/or light. These vessels are appropriate for pharmaceutical use and have volumes from 1 up to 10 ml capable to deliver doses from 25 μg up to 300 μg of levothyroxine Na. The vessels may have the form of an ampoule, sachet, vial, blister pack, tube, or a stick pack made from plastic or glass.

Oral solutions of different concentrations may be obtained using the method described above. The amounts of ingredients are shown in the tables below for solutions containing 5 μg/ml (25 μg in 5 ml), 10 μg/ml (50 μg in 5 ml), and 20 μg/ml (100 μg in 5 ml). The method above may be scaled up or down using techniques known in the art to obtain different quantities and/or concentrations.

TABLE I

25 mg dose

| No | NAME OF INGREDIENTS | FUNCTION | REFERENCE STANDARDS | QUANTITY | UNITS |
|---|---|---|---|---|---|
| | COMPOSITION IN ACTIVE SUBSTANCE(S) | | | | |
| 1. | LEVOTHYROXINE SODIUM | Active ingredient | Ph. Eur. | 25.00 | MCG |
| | COMPOSITION IN EXCIPIENTS AND OTHER INGREDIENTS | | | | |
| 1. | GLYCEROL liquid | Dissolving agent | Ph. Eur. | 2-4 | G |
| 2. | CITRIC ACID | Buffering agent | Ph. Eur. | qs to pH 5.5 | MG |
| 3. | NIPAGIN M sodium | Antimicrobial agent | Ph. Eur. | 0.002-0.009 | G |
| 4. | PURIFIED WATER | Solvent | Ph. Eur. | qs to 5 ml (about 2.00 gr) | G |
| 5. | SODIUM HYDROXIDE 1N | pH adjustment | Ph. Eur. | qs to pH 10 | MG |
| | TOTAL QUANTITY | | | 5.00 | ML |

TABLE II

50 mg dose

| No | NAME OF INGREDIENTS | FUNCTION | REFERENCE STANDARDS | QUANTITY | UNITS |
|---|---|---|---|---|---|
| | COMPOSITION IN ACTIVE SUBSTANCE(S) | | | | |
| 1. | LEVOTHYROXINE SODIUM | Active ingredient | Ph. Eur. | 50.00 | MCG |
| | COMPOSITION IN EXCIPIENTS AND OTHER INGREDIENTS | | | | |
| 1. | GLYCEROL liquid | Dissolving agent | Ph. Eur. | 2-4 | G |
| 2. | CITRIC ACID | Buffering agent | Ph. Eur. | qs to pH 5.5 | MG |
| 3. | NIPAGIN M sodium | Antimicrobial agent | Ph. Eur. | 0.002-0.009 | G |
| 4. | PURIFIED WATER | Solvent | Ph. Eur. | qs to 5 ml (about 2.00 gr) | G |
| 5. | SODIUM HYDROXIDE 1N | pH adjustment | Ph. Eur. | qs to pH 10 | MG |
| | TOTAL QUANTITY | | | 5.00 | ML |

TABLE III

100 mg dose

| NAME OF INGREDIENTS | FUNCTION | REFERENCE STANDARDS | QUANTITY | UNITS |
|---|---|---|---|---|
| COMPOSITION IN ACTIVE SUBSTANCE(S) | | | | |
| LEVOTHYROXINE SODIUM | Active ingredient | Ph. Eur. | 100.00 | MCG |
| COMPOSITION IN EXCIPIENTS AND OTHER INGREDIENTS | | | | |

| No | NAME OF INGREDIENTS | FUNCTION | REFERENCE STANDARDS | QUANTITY | UNITS |
|---|---|---|---|---|---|
| 1. | GLYCEROL liquid | Dissolving agent | Ph. Eur. | 2-4 | G |
| 2. | CITRIC ACID | Buffering agent | Ph. Eur. | qs to pH 5.5 | MG |
| 3. | NIPAGIN M sodium | Antimicrobial agent | Ph. Eur. | 0.002-0.009 | G |
| 4. | PURIFIED WATER | Solvent | Ph. Eur. | qs to 5 ml (about 2.00 gr) | G |
| 5. | SODIUM HYDROXIDE 1N | pH adjustment | Ph. Eur. | qs to pH 10 | MG |
| | TOTAL QUANTITY | | | 5.00 | ML |

Comparative Tests:

The stability of the solutions according to the invention was tested against commercially available levothyroxine solutions prepared using the same ingredients as mentioned in the tables above, differing only in their method of preparation. These commercially available solutions are sold under the brand name Evotrox. Analytical results are shown in table IV.

TABLE IV

| Test | Method | Results BATCHES OF EVOTROX ® ORAL SOLUTION | | |
|---|---|---|---|---|
| | | 25 mcg/5 ml | 50 mcg/5 ml | 100 mcg/5 ml |
| General items | | Lot No: EVT 010 | Lot No: EVR 012 | Lot No: EVX 011 |
| Appearance | Visual examination | amber glass bottle with cap containing a clear viscous liquid* | | |
| Clarity and degree of opalescence of liquids | Ph. Eur. cur. ed. (2.2.1) | clear viscous liquid | | |
| pH value | Ph. Eur. cur. ed. (2.2.3) | 5.6 | 5.6 | 5.6 |
| Relative density | Ph. Eur. cur. ed. (2.2.5) | 1.1 | 1.1 | 1.1 |
| Identity-Assay Identification | Ph. Eur. cur. ed. (2.2.29) | | | |
| Levothyroxine sodium (HPLC) | | Retention time complies with RS | Retention time complies with RS | Retention time complies with RS |
| Sodium methyl paraben (E219) | | Retention time complies with RS | Retention time complies with RS | Retention time complies with RS |
| Assay | Ph. Eur. cur. ed. (2.2.29) | | | |
| Levothyroxine sodium (HPLC) | | 77.2% | 78.9% | 84.0% |
| Purity tests Related substance | | | | |
| Liothyronine | NMT 1.00% | 1.4% | Not performed | 1.40% |
| Single unknown impurities | NMT 1.00% | 10.4% | Not performed | 1.5% |
| Total impurities | NMT 1.00% | 16.2% | Not performed | 3.0% |

Before the tests, all solutions were tested for purity using HPLC. Comparative tests of the pure compositions according to the invention and the EVOTROX solutions were done under normal controlled and stress conditions.

Table V shows the results for the Evotrox solutions:

TABLE V

| 25 µg/5 ml solutions stability | | | |
|---|---|---|---|
| after 1 month forced studies | RESULTS | | |
| Conditions | normal | 40° C. | 70° C. |
| Appearance | Clear viscous solution with floating particles in some samples* | | |
| pH | 5.5 | | |
| Assay | 77.2% | — | — |
| Liothyronine | 1.4% | — | — |
| Major unspecified impurity | 10.4% | — | — |
| Total unspecified impurities | 16.2% | — | — |
| Glycerol | ~500 g/L | | |
| Package | Brown glass bottles holding 100 ml of solution | | |

*most of the evotrox ® samples had floating particles even before we placed them for pre-stability studies in the oven.
Test and results of Evotrox ® 25 microgram/5 ml Oral Solution

TABLE VI

Test and results of Evotrox ® 100 microgram/5 ml Oral Solution

| after 1 month forced studies | RESULTS | | |
|---|---|---|---|
| Conditions | normal | 40° C. | 70° C. |
| Appearance | Clear viscous solution with floating particles in some samples* | | |
| Assay | 84.0% | 73.4% | — |
| Liothyronine | 1.4% | 4.8% | — |
| Major unspecified impurity | 1.5% | 3.4% | — |
| Total unspecified impurities | 3.0% | 5.4% | — |
| Glycerol | ~500 g/L | | |
| Package | Brown glass bottles holding 100 ml of solution | | |

*most of the evotrox ® samples had floating particles even before we placed them for pre-stability studies in the oven.
Test and results of Evotrox ® 100 microgram/5 ml Oral Solution

TABLE

100 μg/5 ml solutions

| | PHARMA-DATA 100 MCG/5 ML | | Evotrox ® EVX011 | |
|---|---|---|---|---|
| PARAMETERS | normal | 40° C. | normal | 40° C. |
| after 2 months forced studies | | | | |
| Appearance | clear solution | | Almost clear | |
| Final pH | 5.5 | | 5.6 | |
| Assay | 106.4% | 104.4% | 85.2% | 73.4% |
| Liothyronine | 0.19% | 0.77% | 0.81% | 4.8% |
| Any unspecified impurity | 0.12% | 0.8% | 1.4% | 3.4% |
| Total other unspecified impurities | 0.28% | 1.1% | 3.4% | 5.4% |
| after 6 months forced studies | | | | |
| Appearance | clear solution | | Almost clear | |
| Final pH | 5.5 | | 5.6 | |
| Assay | 103.9% | 99.1% | 80.8% | 65.8% |
| Liothyronine | 0.16% | 2.4% | 1.6% | 6.5% |
| Any unspecified impurity | 0.07% | 0.34% | 1.3% | 9.6% |
| Total other unspecified impurities | 0.35% | 0.65% | 3.8% | 11.2% |

In both the 25 μg/5 ml and 100 μg/5 ml solutions, the levothyroxine solutions prepared using the method according to the invention show significantly less impurities after 2 months under normal or stress conditions. Thus it is concluded the solutions prepared according to the invention have a higher stability during storage, even though the constituents of the starting solutions were virtually the same according to HPLC analysis.

The invention claimed is:

1. A method for the preparation of an oral levothyroxine composition, the method comprising the steps of:
   a) providing a salt of levothyroxine,
   b) mixing levothyroxine with an aqueous solvent,
   c) adjusting the pH to a pH of at least 8 to yield a basic aqueous solvent,
   d) dissolving the levothyroxine in the basic aqueous solvent to yield a levothyroxine solution, and
   e) lowering the pH of the clear levothyroxine solution to between 5-6.

2. The method according to claim 1, where in step c) the pH is adjusted to from 9 to 11.

3. The method according to claim 1, wherein the adjusting of the pH in step c) is done by adding a base.

4. The method according to claim 3, wherein the added base is a sodium hydroxide solution.

5. The method according to claim 1, wherein the adjusting of the pH in step e) is done using a carboxylic acid.

6. The method according to claim 4, wherein the carboxylic acid is citric acid.

7. The method according to claim 1, wherein the aqueous solvent is a mixture of water and a water-miscible organic solvent or solubilizer.

8. The method according to claim 6, wherein the water-miscible organic solvent comprises glycerol.

9. The method according to claim 7, wherein the ratio between water and glycerol is in the range of 10:1 to 1:10.

10. The method according to claim 1, where in step b) levothyroxine is mixed with the aqueous solvent while heating the mixture to 30-70° C.

11. The method according to claim 1, wherein the aqueous solvent further comprises a preservative.

12. The method according to claim 11, wherein the preservative is sodium methylparaben.

13. The method according to claim 1, wherein the salt of levothyroxine is the sodium salt.

14. An oral Levothyroxine composition according to claim 1, wherein the composition comprises a sodium levothyroxine concentration of approximately 25μg in 5 ml, approximately 50μg in 5 ml or approximately 100μg in 5 ml, wherein the composition comprises sodium levothyroxine, glycerol, water and a preservative.

15. The oral Levothyroxine composition according to claim 14, wherein the composition is packed in a unit dose system selected from the group consisting of ampoules, sachets, vials, blister packs, tubes, or stick packs, wherein the unit dose is arranged to deliver separate doses of levothyroxine from 25 up to 300mcg per single dose.

* * * * *

UNITED STATES PATENT AND TRADEMARK OFFICE
CERTIFICATE OF CORRECTION

PATENT NO. : 9,050,307 B2  
APPLICATION NO. : 14/003598  
DATED : June 9, 2015  
INVENTOR(S) : Psarrakis et al.

Page 1 of 1

It is certified that error appears in the above-identified patent and that said Letters Patent is hereby corrected as shown below:

Title page (73), in "Assignee", in column 1, line 1, delete "GmbH" and insert --GmbH, Zürich--, therefor

Claims

In column 10, line 31, in Claim 10, delete "30-70° C." and insert --30-70 °C.--, therefor In column 10, line 40, in Claim 14, delete "25μg" and insert --25 μg--, therefor In column 10, line 41, in Claim 14, delete "in" and insert --is--, therefor In column 10, line 41, in Claim 14, delete "in" and insert --is--, therefor Signed and Sealed this  
Twelfth Day of April, 2016

Michelle K. Lee  
*Director of the United States Patent and Trademark Office*

UNITED STATES PATENT AND TRADEMARK OFFICE
CERTIFICATE OF CORRECTION

PATENT NO.       : 9,050,307 B2
APPLICATION NO.  : 14/003598
DATED            : June 9, 2015
INVENTOR(S)      : Psarrakis et al.

It is certified that error appears in the above-identified patent and that said Letters Patent is hereby corrected as shown below:

Claims

In column 10, line 41, in Claim 14, delete "50μg" and insert --50 μg--, therefor In column 10, line 41, in Claim 14, delete "is" and insert --in--, therefor In column 10, line 41, in Claim 14, delete "100μg" and insert --100 μg--, therefor In column 10, line 41, in Claim 14, delete "is" and insert --in--, therefor Signed and Sealed this
Second Day of August, 2016

Michelle K. Lee
*Director of the United States Patent and Trademark Office*